United States Patent [19]

Massot et al.

[11] Patent Number: 4,705,780

[45] Date of Patent: Nov. 10, 1987

[54] MEDICAMENTS CONTAINING PICHIA OR EXTRACTS THEREOF

[75] Inventors: Jacqueline O. Massot, Seine-et-Marne; Jaques N. Astoin, Paris, both of France

[73] Assignee: Univablot, Paris, France

[21] Appl. No.: 889,281

[22] Filed: Jul. 24, 1986

Related U.S. Application Data

[63] Continuation of Ser. No. 680,579, Dec. 11, 1984, abandoned, which is a continuation-in-part of Ser. No. 619,887, Jun. 12, 1984, abandoned, which is a continuation-in-part of Ser. No. 315,498, Oct. 27, 1981, abandoned, which is a continuation of Ser. No. 114,327, Jan. 22, 1980, abandoned.

[30] Foreign Application Priority Data

Jan. 25, 1979 [FR] France ................. 79 01879

[51] Int. Cl.$^4$ ........................... A61K 31/715
[52] U.S. Cl. ..................................... 514/54
[58] Field of Search ........................... 574/54

[56] References Cited

PUBLICATIONS

Bell et al., J. Chem. Soc., (1950), pp. 1944–1947.
Massot et al., Bull. Soc., Fr. MgCo Med 6(1), 1977, pp. 45–48.
Sandula et al., Folia Microbiological, 21(3), 1976, p. 188.
Peat et al., J. Chem. Soc., (1958), pp. 3862–3870.
Manners et al., J. Gen. Micro., 1974, 88:411–417.

*Primary Examiner*—Johnnie R. Brown
*Assistant Examiner*—John W. Rollins, Jr.
*Attorney, Agent, or Firm*—Wegner and Bretschneider

[57] ABSTRACT

Pichia or extracts of Pichia may be used in the treatment of human beings and animals for the purpose of non-specific immunostimulation, potentiation of the action of antibiotics and increasing vaccine activity.

7 Claims, No Drawings

MEDICAMENTS CONTAINING PICHIA OR EXTRACTS THEREOF

CROSS REFERENCE TO RELATED APPLICATIONS

This application is a continuation of U.S. application Ser. No. 680,579, filed Dec. 11, 1984, now abandoned, which is a continuation-in-part of Ser. No. 619,887, filed June 12, 1984, now abandoned, which in turn is a continuation-in-part of Ser. No. 315,498, filed Oct. 27, 1981, now abandoned, which in turn is a continuation of Ser. No. 114,327, filed Jan. 22, 1980, now abandoned.

The present invention relates to the use of Pichia, in particular *Pichia fermentans,* or extracts of Pichia as such, as a medicament.

Pichia is a yeast belonging to the Saccharomycetaceae family and to the Saccharomycoideae sub-family comprising numerous genera. These genera are defined for example in "The Yeasts" (LODDER, North Holland Publishing Company, 1970, pages 405 to 554). The species *Pichia fermentans,* which has been more especially studied by the Applicants, is known and can be obtained form several collections of microorganisms, for example from the CENTRAALBUREAU VOOR SCHIMMEL CULTURES (DELFT, Netherlands), under No. CBS 187.

To the Applicants' knowledge, Pichia has never been studied with a view to therapeutic use. Yeasts belonging to a different genus, such as *Saccharomyces cerevisiae,* have been used in therapeutic applications, in particular as protective or regenerative agents for the intestinal bacterial flora.

Moreover, certain authors have studied extracts of *Saccharomyces cerevisiae* or their glucanes as regards their effect on the reticulo-endothelial system (RIGGI and Di Luzio, Am J. Physiol. (1961) 200, 2, pages 297-300) or as regards their anti-tumor action (HAMURO and colleagues, C.A., (1978), 89, 40 704 b).

Now, the Applicants have found that Pichia, notably *Pichia fermentans* as well as its extracts, in particular the insoluble glucanes, have exceptional pharmacological properties that justify their use as medicaments in the treatment of infectious diseases: non-specific immunostimulation, potentialisation of the action of antibiotics, and increase in the activity of vaccines.

The Pichia strains may be cultivated and grown in a known manner on culture and fermentation media conventionally used for yeasts. The cells obtained may be dried at 50° in vacuo, but are preferably lyophilised (freeze dried).

The extracts according to the invention, which are in principle insoluble glucanes, may be isolated from the cell walls of Pichia, for example by the method described by Bell and Northcote (J. Chem. Soc. (1950), p. 1944–47), if necessary modified, for example according to Peat and colleagues (idem, 1958a, p. 3862–3868). The principle consists of removing first the proteins, lipids and mannans by alkaline treatment (for example with a diluted strong alkali such as sodium hydroxide), and then the glycogen and the soluble glucanes by acid treatment (for example with acetic or hydrochloric acid), from the cellular mass obtained by fermentation. The extract may be dried by atomization.

The following examples illustrate the preparation of these products.

EXAMPLE 1

Process for fermenting *Pichia fermentans*

(a) Preparation of yeast sediments

The yeast sediment (the sediment placed in the bottom of the vat to start fermentation) is prepared from the stock culture for the *Pichia fermentans* strain. The latter is obtained by incubating yeast for 48 hours at 30° C. on sloped agar containing:

| Medium (1) | yeast water | 500 ml |
|---|---|---|
| | pancreatic peptone | 2 g |
| | starch syrup | 10 g |
| | agar | 18 g |
| | tap water, in an amount sufficient to make up | 1 liter. |

The culture is separated from the sloped agar via a tube, using about 10 ml of sterile physiological serum. The suspension thus obtained is added, while maintaining sterile conditions, to a 6-liter volume Erlenmeyer flask containing 1.5 liter of fermentation medium of the following composition:

| Medium (2) | glucose | 10 g |
|---|---|---|
| | yeast extract | 2 g |
| | ammonium sulphate | 5 g |
| | monopotassium phosphate | 5 g |
| | magnesium sulphate (7 H$_2$O) | 0.05 g |
| | calcium chloride | 0.01 g |
| | ferrous sulphate (7 H$_2$O) | 0.01 g |
| | potassium chloride | 0.01 g |
| | tap water, sufficient to make up | 1 liter. |

Incubation is carried out for 24 hours at 27°±1° in a rotary agitator operating at about 115 revs./minute.

(b) Fermentation

The contents of the Erlenmeyer flask as obtained above (about 3 liters) are inoculated in a sterile fermentation vat containing 100 liters of medium (2) described above. Fermentation is carried out for 20 hours while aerating at a rate of 20 m$^3$/hour. The contents of the vat are then centrifuged in order to collect the mass containing the Pichia cells.

2.8 kg of a cellular mass are obtained (74% moisture).

EXAMPLE 2

Preparation of desiccated *Pichia fermentans* cells 255 g of cells ready for use are obtained by drying in vacuo at 50° C. 1 kg of the cellular mass obtained in Example 1.

An alternative, which can be used in order to obtain a product that is easier to store and use, is as to lyophilise the cellular mass obtained in Example 1; in this way 252 g of utilisable cells are obtained from 1 kg of cellular mass.

EXAMPLE 3

Preparation of glucanes of *Pichia fermentans*

1 kg of freshly centrifuged cellular material obtained according to Example 1 is treated with 3 liters of a 6% sodium hydroxide solution for 1½ hours at 80° C.; the residue is collected by centrifugation (4000 revs./minute for 15 minutes) and is then treated with 5 liters of a 3% sodium hydroxide solution for 18 hours at ambient temperature. The solution is recentrifuged and the insoluble product is retreated with a 3% sodium hydroxide solution for 2 hours at 80° C. The solution is centrifuged and the centrifuge deposit is taken up in 3 liters of water. The suspension thus obtained is adjusted to a pH of 4.5 with acetic (or hydrochloric) acid and is heated at 80° C. for 2 hours while stirring. The residue obtained by centrifugation is washed 3 times with 1 liter of boiling water each time, is taken up in 2.5 liters of a 0.02M sodium acetate solution, and is then autoclaved at 1 bar atmosphere for 1½ hour.

The insoluble fraction is washed with water, then with ethanol and acetone, and is dried in vacuo at a maximum temperature of 50° C. The product obtained is ground and provides 15.5 g of a cream colored powder.

An alternative method is lyophilisation, and 14.2 g of extract can be obtained starting from the same quantity of cells.

A further method is atomization, and 15.3 g of extract can be obtained starting from the same quantity of cells. This extract has a particle size between 5 and 30μ, which enables use without further treatment.

Analysis: C=45.15%; H=7.42%; O=47.4% N<0.2% P: absent.

The action of pancreatic amylase on the extract releases only a few traces of reducing compounds, thus indicating the absence of glycogen.

The extract according to the invention is remarkable in that it is insoluble in water, alkaline or acid diluted solutions, and the usual organic solvents such as ethanol, diethyl ether, ethyl acetate, acetone, chloroform, etc.

It is found however that it is very slightly soluble in dimethyl sulphoxide (DMSO).

Specific rotary power: $|\alpha|_D^{20} \cong -60°$ (C=0.2; DMSO).

Infra-red: the spectrum obtained using a KBr prism has a characteristic absorption band at 885 cm$^{-1}$.

The presence of such IR absorption band is proof that the Pichia extract contains β bonds and specifically β1—3 bonds. The partial hydrolysis of the extract confirms the presence of a major part of β1—3 bonds and also of some β1—6 bonds.

According to the methylation test (Hakomori method, Methods of Enzymology 28 178-195, 1972), the observed presence of sugar bonded in $\neq$1—3—6 means that the Pichia extract in fact has a branched structure, which is believed to correspond to the following formula (presumed formula):

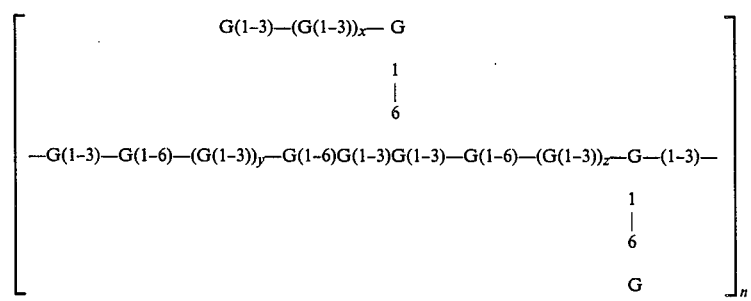

in which
G=glucose unit,
x+y+z=about 40 and
n=about 26.

It is to be noted that the above formula does not indicate the exact position of the β1—6 bonds within the chains, which simply have been placed so that the above proportion (one β1—6 bond for 9 to 10 glucose units) is satisfied.

The polymerization degree as determined according to the method of Manners et al. (Manners, Masson, Patterson, Carbohyd. Res. 17 (1971) 109-104), is 1320 (±100) which corresponds to a molecular weight of about 200,000 to 230,000.

Thus the Pichia extract according to the invention, which will be called "glucans" hereafter in the text, consists essentially of branched β (1—3)- and β (1—6)-D-glucans comprising about one β (1—6) bond for 9 to 10 glucose units, said glucans having a molecular weight of about 200,000 to 230,000.

The Pichia yeasts, in particular *Pichia fermentans* as well as the glucanes extracted therefrom, have been subjected to pharmacological tests.

TOXICITY

No toxicity was observed when *Pichia fermentans* or its glucanes were administered orally to mice.

The LD$_{50}$ of these glucanes administered intraperitoneally is greater than 500 mg/kg.

Evidence of immunostimulation produced by whole cells of Pichia and by its glucanes 1—Whole cells of *Pichia fermentans* admininstered orally

Preventive and curative treatment

The animals used were female IOPS IFFA CREDO mice weighing 18-20 grams and fed for one week before the test on a diet containing no yeast but containing the necessary dosage of vitamins.

The mice were split up into 2 batches each containing 10 animals:
1 infected control batch
1 infected batch treated with Pichia.

The animals were infected intravenously with a highly pathogenic strain of *Staphylococcus aureus* (Institut Pasteur Strain No. 54 146), and the *Staphylococcus aureus* used was reactivated by being passed through mice before the test. A culture in nutrient broth incubated for 16 hours at 37° C. was diluted to 1/100 and then used to infect the mice. Each mouse received intravenously, under these conditions, about 6×10$^5$ virulent germs.

The experimental schedule was as follows:

|  | Control batch | Treated batch |
| --- | --- | --- |
| Day - 3 | 0.2 ml of physiological serum administered orally to each mouse | 0.2 ml of a suspension of Pichia containing |
| Day - 2 |  |  |

-continued

| | Control batch | Treated batch |
|---|---|---|
| Day - 1 | | 3 g/20 ml, administered orally to each mouse |
| Day - 0 | STAPHYLOCOCCAL INFECTION by intravenous route | |
| Day 0 to Day + 7 | the same as day - 3 to day - 1 | the same as day - 3 to day - 1 |

The number of dead mice in each batch is noted every day. This test was carried out 5 times and the following results, expressed in terms of the number of surviving mice, were obtained.

| | Control batch | Treated batch |
|---|---|---|
| Test No. 1 | 1/10 | 3/10 |
| Test No. 2 | 3/10 | 10/10 |
| Test No. 3 | 1/10 | 2/10 |
| Test No. 4 | 3/10 | 1/10 |
| Test No. 5 | 0/10 | 6/10 |
| % survival | 16% | 44% |

As can be seen, the number of dead mice in the treated batch is less than the number of dead mice in the control batch.

In view of the virulence of the injected pathogen, a substantial protection is conferred by the oral administration of Pichia.

This protection can be attributed to a non-specific immunostimulation.

2—Whole cells of Pichia and its glucanes admininstered intraperitoneally

Preventive treatment

The animals used were female IOPS IFFA CREDO mice weighing 18-20 grams, fed for 8 days before the test on a diet free from yeasts but containing the necessary amount of vitamins.

The mice were divided into 2 batches:
1 infected control batch
1 infected batch treated either with Pichia or with its glucanes.

The tests were carried out on mice infected intravenously with about $1 \times 10^6$ *Staphylococcus aureus* pathogens (Institut Pasteur Strain 54.146) prepared as described previously.

The treatment was given intraperitoneally.
for *Pichia fermentans*, in a dosage of 50 mg/kg
for the glucanes of *Pichia fermentans*, in a dosage of 10 mg/kg.

The experimental schedule was as follows:

| | Control batch | Treated batch |
|---|---|---|
| Day - 7 | Intraperitoneal injection of 0.2 ml of physiological serum per mouse | Intraperitoneal injection of 0.2 ml of a suspension of Pichia or glucanes |
| Day - 4 | 2nd injection, as above | 2nd injection, as above |
| Day 0 | Staphylococcal infection by intravenous route | |

The number of dead mice in each batch is noted every day.

The following tables show the number of surviving animals for several tests.

| (A) - with whole cells of *Pichia fermentans* | | |
|---|---|---|
| | Control batch | Treated batch |
| Test No. 1 (on 10 mice) | 2 | 6 |
| Test No. 2 (on 5 mice) | 1 | 5 |
| Test No. 3 (on 10 mice) | 0 | 8 |
| % survival | 12% | 76% |

| (B) - with glucanes of Pichia | | |
|---|---|---|
| | Control batch | Treated batch |
| Test No. 1 (on 10 mice) | 1 | 9 |
| Test No. 2 (on 5 mice) | 0 | 3 |
| Test No. 3 (on 10 mice) | 0 | 8 |
| Test No. 4 (on 10 mice) | 2 | 7 |
| % survival | 8.5% | 77.2% |

As can be seen, the number of dead mice is less in the treated batches than the number of dead mice in the control batches, whether treatment is effected with whole cells of *Pichia fermentans* or its glucanes.

Given the virulence of the injected pathogen, intraperitoneal injection of Pichia or its glucanes confers a high degree of protection.

This protection can be attributed to a non-specific immunostimulation.

Cultures of Pichia kluyveri (ATCC 9768), Pichia membranae faciens (ATCC 26288 and CBS 107) and Pichia polymorpha (ATCC 18577 and CBS 6.2) are grown and treated in the same manner as described above in Example 1 for Pichia fermentans. Whole cells of Pichia are lyophilized as in Example 2 above, and glucanes thereof are obtained by the process of Example 3 above. The immunostimulative effect produced through oral treatment is tested by the method described previously. The results are shown in the table below:

| | Control batch | *Pichia kluyveri* ATCC 9768 | *Pichia membranae faciens* ATCC 26288 | *Pichia polymorpha* ATCC 18577 |
|---|---|---|---|---|
| Test No. 1 | 2/10 | 4/10 | 3/10 | 4/10 |
| Test No. 2 | 1/10 | 3/10 | 3/10 | 3/10 |
| Test No. 3 | 1/10 | 5/10 | 6/10 | 4/10 |
| Test No. 4 | 0/10 | 5/10 | 1/10 | 2/10 |
| Test No. 5 | 3/10 | 4/10 | 5/10 | 6/10 |
| % survival | 14% | 42% | 36% | 38% |

The immunostimulative effect produced through intraperitoneal treatment is tested by the method described previously. The results are shown in the table below:

| | Control Batch | ATCC 9768 | ATCC 26288 | ATCC 18577 |
|---|---|---|---|---|
| Test No. 1 | 1/10 | 7/10 | 6/10 | 8/10 |
| Test No. 2 | 2/10 | 8/10 | 8/10 | 8/10 |
| Test No. 3 | 0/10 | 7/10 | 6/10 | 5/10 |

-continued

| % survival | Control Batch | ATCC 9768 | ATCC 26288 | ATCC 18577 |
|---|---|---|---|---|
| % survival | 10% | 73% | 67% | 70% |

Evidence of immunostimulation by Pichia glucanes following the prior injection of an antigen The animals used were female SPF IFFA-CREDO mice weighing 18-20 grams, fed for one week before the tests on a diet free from yeast but containing the necessary dosage of vitamins.

These mice were divided into 4 batches each containing 10 mice.
batch 1: infected control batch
batch 2: antigen control batch ("vaccine")
batch 3: received the specific antigen and were also infected
batch 4: as per batch 3, but treated in addition with Pichia glucanes.

The antigen in this case is a *Staphylococcus aureus* culture (Institut Pasteur 54.146) administered in a nonlethal dosage.

The culture is grown for 16 hours in nutrient broth and is then diluted immediately before vaccination to $1 \times 10^{-4}$, representing about $1 \times 10^4$ germs/ml.

The mice of batches 1, 3 and 4 were infected with a highly pathogenic strain of reactivated *Staphylococcus aureus* (Institut Pasteur 54.146). A nutrient broth culture incubated for 16 hours at 37° was injected undiluted and intravenously to infect the mice (i.e. $1 \times 10^8$ germs/ml).

The experimental schedule was as follows:

| | Batch 2 control + Antigen | Batch 1 infection control | Batch 3 vaccinated + infected | Batch 4 vaccinated + infected + Glucanes |
|---|---|---|---|---|
| Day -9 | 0.2 ml of $10^4$ germs/ml administered I.V. | 0.2 ml of physiological serum administered I.V. | 0.2 ml of $10^4$ germs/ml administered I.V. | 0.2 ml of $10^4$ germs/ml administered I.V. |
| Day -6 Day -5 Day -4 Day -3 Day -2 Day -1 | 0.2 ml of physiological serum administered I.V. per day | 0.2 ml of physiological serum administered I.V. per day | 0.2 ml of physiological serum administered I.V. per day | 0.2 ml of 10 mg/kg/day of glucanes administered intraperitoneally |
| Day 0 | 0.2 ml of physiological serum administered I.V. | infection by intravenous route (0.2 ml of culture containing $10^8$ germs/ml) | | |

The number of dead mice in each batch is noted every day. The following table gives the survival rate as a function of time.

| DAYS AFTER INFECTION | Batch 1 infection control | Batch 2 Antigen control | Batch 3 Antigen + infection | Batch 4 Antigen + infection + Glucanes |
|---|---|---|---|---|
| 1st day | 0/10 | 10/10 | 9 | 10 |
| 2nd day | | | 7 | 9 |
| 3rd day | | | — | — |
| 4th day | | | 3 | 3 |
| 5th day | | | — | — |
| 6th day | | | 1 | — |
| 7th day | | | — | — |
| 8th day | | | 0 | — |
| End of test | 0/10 | 10/10 | 0/10 | 3/10 |

100% of the animals infected with a superlethal dose of *Staphylococcus aureus* were dead within 24 hours.

The animals that had been vaccinated once 9 days before the superlethal infection are slightly protected since they all die only after 8 days.

As may be seen from the results in the tables, treatment by glucanes administered intraperitoneally in addition to vaccination protects the animals not only by increasing the survival time but also by reducing the mortality rate.

Given the very high degree of virulence of the injected pathogen, the potentialization conferred by the glucanes on a specific prevaccination is quite considerable. This potentialization can in this case also be attributed to an immunostimulation.

Evidence of the potentialization of the action of antibiotics

In this test, a therapeutic treatment for 2 days using glucanes in a dosage of 10 mg/kg was combined with a short-term course of antibiotic treatment (single injection of penicillin) in a normal therapeutic dosage (30,000 units/kg).

The animals used were the same strain as in the previous tests, and were fed on the same diet.

The mice were divided into 4 batches each containing 5 mice:
batch 1: infection control
batch 2: treated with Pichia glucanes
batch 3: received 1 injection of penicillin
batch 4: received Pichia glucanes and 1 injection of penicillin.

The test was carried out on mice infected intravenously with about $1 \times 10^6$ reactivated *Staphylococcus aureus* pathogens (Institut Pasteur 54.146).

A culture in nutrient broth incubated for 16 hours at 37° C. as diluted to 1/100 and used to infect the mice.

The experimental schedule was as follows:

| | Infection control | Glucanes | Penicillin | Penicillin + glucanes |
|---|---|---|---|---|
| Day 0 | STAPHYLOCOCCAL INFECTION BY INTRAVENOUS ROUTE | | | |
| Day +1 | nothing | Intraperitoneally: 0.2 ml of a suspension of glucanes, 10 mg/kg | Intramuscularly: 0.2 ml of a solution of penicillin, 30,000 IU/kg | Intraperitoneally: 0.2 ml of a suspension of glucanes containing 10 mg/kg + intramuscularly, 0.2 ml of a solution of penicillin, 30,000 IU/kg |
| Day +2 | nothing | Intraperitoneally: 0.2 ml of a suspension of glucanes, | nothing | intraperitoneally: glucanes |

-continued

| | Infection control | Glucanes | Penicillin | Penicillin + glucanes |
|---|---|---|---|---|
| | | 10 mg/kg | | |

The number of dead mice is noted every day, and the following table gives the number of surviving mice observed in each batch.

| Controls | Glucanes alone | Penicillin alone | Glucanes + Penicillin |
|---|---|---|---|
| 1/5 | 3/5 | 2/5 | 4/5 |

As before, protection is conferred by Pichia glucanes alone, although used as a therapeutic treatment in this test (3/5).

Penicillin conferred a slight protection on the animals (2/5).

The combination of glucanes with the same dosage of penicillin potentialized the antibiotic action of the latter (4/5).

The tests described above show that the administration of *Pichia fermentans* or its glucanes on the one hand reduces, by non-specific immunostimulation, the mortality rate in animals infected with a pathogen, and on the other hand potentializes the action of antibiotics and vaccines. This yeast can thus be used to reinforce the resistance of an organism to infectious agents and to improve the immune defense system.

Since the *Pichia fermentans* yeasts and glucanes extracted therefrom are non-toxic, they may be used in the prevention and/or treatment of acute or chronic infectious diseases, in particular diseases of the oto-rhino-laryngeal and/or pulmonary systems, but may also be used to treat any other illness of viral or bacterial origin.

Pichia fermentans and its glucanes may be used as medicaments alone or in combination with one or more antibiotics.

The whole cells of Pichia may be administered orally in daily dosages of 100 to 2000 mg (dry product) per day, preferably in capsules containing the lyophilised cells and, if desired, with convention excipients, or as ampules for oral consumption, the cells being suspended in their culture medium.

| Example of the composition of a capsule: | |
|---|---|
| Lyophilised cells of *Pichia fermentans* | 50 mg |
| Lactose | 7 mg |
| Magnesium stearate | 2 mg |
| Icing sugar in an amount to make a capsule containing | 150 mg |

The Pichia glucanes may also be administered orally (a gastroresistant form) in daily dosages of 20 to 500 mg, preferably 50-200 mg, or may also be used in the form of injectable suspensions in an amount of 5 to 100 mg per day. The use of these glucanes in the form of skin creams or aerosols may also be considered. An aerosol dosage of about 5-50 mg per day, preferably 5-10 mg per day, is contemplated. The contemplated treatment involves daily dosages for 5 to 8 days, repeated after one week if necessary. The oral form is contemplated for general use in treating infectious diseases. The aerosol form is contemplated for treatment of diseases of the upper respiratory and pulmonary system, particularly for immuno-depressed subjects, such as post-operative, radiation treatment and burn victim situations or those suffering from chronic respiratory diseases.

Example of the composition of an injectable suspension:

| | |
|---|---|
| Micronized glucanes of *Pichia fermentans* (particles < 50 μm, of which 80% < 10 μm) | 0.010 g |
| Polysorbate 80 | 0.025 g |
| Polyvinyl pyrrolidone | 0.025 g |
| Monosodium phosphate | 0.025 g |
| Sodium chloride, in an amount sufficient to produce an isotonic solution | |
| Sodium merthiolate | 0.0002 g |
| Non-pyrogenic distilled water, in an amount sufficient for 1 5 ml ampule for injection | |

Example of an aerosol

| | |
|---|---|
| Micronized glucanes (particles < 50 μm, of which 80% < 10 μm) | 0.050 g |
| Polysorbate 80 | 0.2 g |
| Polyoxyethylenated oleic glycerides | 1 g |
| Monosodium phosphate | 0.1 g |
| Sodium chloride in an amount sufficient to give an isotonic solution | |
| Sodium merthiolate | 0.0008 g |
| Purified water, in an amount sufficient to make | 20 ml |

Example of the composition of an oral form

This form consists in neutral microgranules on which micronized glucanes are fixed and which are protected by three successive Eudragit L coatings. The composition of said form is as follows:

| | |
|---|---|
| Micronized glucanes | 10 g |
| Neutral microgranules | 20 g |
| Talc | 3 g |
| Polyethyleneglycol 6000 (PEG 6000 MW - about 5600-7000) | 1 g |
| Erythrosine lake (40% FDC) | 0.15 g |
| Eudragit L (an anionic polymer of methacrylic acid and methyl methacrylate dissolved in isopropanol and produced by Rohm Pharma) | 25 g |

The neutral microgranules may be a 70/30 mixture of sucrose and starch on which the active substance is applied by successive coatings. An example of a suitable material is that sold under the trademark "NUPAREL" by Edward Mendell, Inc.

What is claimed is:

1. A process for treating bacterial or viral infection, comprising oral administration to a patient in need thereof of about 20-500 mg/day of a water-insoluble Pichia glucan having a molecular weight in the range of about 200,000 to 230,000, consisting essentially of branched beta (1—3) and beta (1—6)-D-glucans having one beta (1—6) bond for 9 to 10 glucose units, substantially free from: (i) proteins, lipids and mannans capable of removal by dilute alkaline treatment; and (ii) glycogens and soluble glucans capable of removal by adjusting the pH to between about 2 to 5 with a strong acid treatment.

2. A process for treating bacterial or viral infection, comprising parenteral administration to a patient in need thereof of about 5-100 mg/day of an injectable suspension Pichia glucan having a molecular weight in the range of about 200,000 to 230,000, consisting essentially of branched beta (1—3) and beta (1—6)-D-glucans having one beta (1—6) bond for 9 to 10 glucose units, substantially free from: (i) proteins, lipids and mannans capable of removal by dilute alkaline treatment; and (ii) glycogens and soluble glucans capable of removal by adjusting the pH to between about 2 to 5 with a strong acid treatment.

3. A composition for treating bacterial or viral infection, comprising an anti-infectively effective amount of a water-insoluble Pichia glucan having a molecular weight in the range of about 200,000 to 230,000, consisting essentially of branched beta (1—3) and beta (1—6)-D-glucans having one beta (1—6) bond for 9 to 10 glucose units, substantially free from: (i) proteins, lipids and mannans capable of removal by dilute alkaline treatment; and (ii) glycogens and soluble glucans capable of removal by adjusting the pH to between about 2 to 5 with a strong acid treatment.

4. A composition according to claim 3, containing 20-500 mg of the glucans in an oral dosage form.

5. A composition according to claim 3, containing 5-100 mg of the glucans, in an injectable suspension.

6. A composition according to claim 3 in aerosol form.

7. A composition according to claim 3, wherein the glucan is extracted from *Pichia fermentans*.

* * * * *